United States Patent
Buchmann et al.

Patent Number: 5,756,818
Date of Patent: May 26, 1998

[54] 9-CHLORO-PROSTAGLANDIN DERIVATIVES

[75] Inventors: Bernd Buchmann, Hohen Neuendorf; Werner Skuballa, Berlin, both of Germany

[73] Assignee: Schering Aktiengesellschaft, Berlin, Germany

[21] Appl. No.: 605,142

[22] PCT Filed: Aug. 29, 1994

[86] PCT No.: PCT/EP94/02855

§ 371 Date: May 29, 1996

§ 102(e) Date: May 29, 1996

[87] PCT Pub. No.: WO95/06634

PCT Pub. Date: Mar. 9, 1995

[30] Foreign Application Priority Data

Aug. 31, 1993 [DE] Germany .................. 43 30 177.0

[51] Int. Cl.$^6$ .................................. C07C 177/00
[52] U.S. Cl. .................. 560/121; 560/115; 562/503; 562/500; 514/530; 514/573
[58] Field of Search .................. 560/121, 115; 562/503, 500; 514/530, 573

[56] References Cited

FOREIGN PATENT DOCUMENTS 030377  6/1981  European Pat. Off. .

08585  4/1994  WIPO .

Primary Examiner—Paul J. Killos
Attorney, Agent, or Firm—Millen, White, Zelano, & Branigan, P.C.

[57] ABSTRACT

The invention relates to 9-chloro-prostaglandin derivatives of formula I

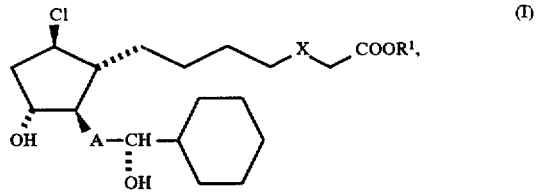

in which X means oxygen or $CH_2$, $R^1$ means hydrogen or straight-chain or branched alkyl with 1–6 C atoms and A means trans-CH=CH— or —$CH_2$—$CH_2$—, as well as their salts with physiologically compatible bases, if $R^1$ represents hydrogen, and their clathrates with α-, β- or γ-cyclodextrin, process for their production and their pharmaceutical use.

12 Claims, No Drawings

9-CHLORO-PROSTAGLANDIN DERIVATIVES

Object of the invention are 9-chloro-prostaglandin analogues, process for their production, as well as their use as pharmaceutical agents.

It is known concerning the extensive prior art of prostaglandins and their analogues that this family of substances is suitable for treating mammals, including humans, because of its biological and pharmacological properties. Their use as pharmaceutical agents encounters difficulties, however. Most natural prostaglandins have too short a duration of action for therapeutic purposes, since they are degraded too quickly by various enzymatic processes. All structural changes therefore have the object of increasing both the duration of action and the selectivity of the action.

It has now been found that the new 9-chloro-prostaglandin analogues have a high-action specificity, better effectiveness, prolonged duration of action and first and foremost greater stability than the natural prostaglandins.

The invention relates to 9-chloro-prostaglandin derivatives of formula I

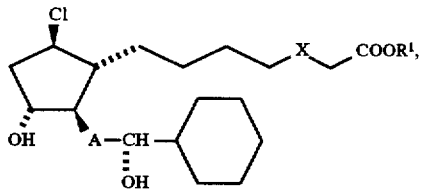

in which

X means oxygen or $CH_2$, $R^1$ means hydrogen or straight-chain or branched alkyl with 1–6 C atoms and A means trans-CH=CH— or —$CH_2$—$CH_2$—, as well as their salts with physiologically compatible bases, if $R^1$ represents hydrogen, and their clathrates with α-, β- or γ-cyclodextrin.

As alkyl radicals $R^1$, R2 and $R^3$, straight-chain or branched $C_1$–$C_6$ alkyl radicals, such as methyl, ethyl, propyl, isopropyl, butyl, isobutyl, tert-butyl, pentyl, isopentyl, neopentyl, hexyl, isohexyl, etc., are suitable.

As physiologically compatible bases, e.g., lyes such as KOH, NaOH or alkaline-earth hydroxides such as $Ca(OH)_2$ are suitable.

The invention further relates to a process for the production of 9-chloro-prostaglandin analogues of formula I, characterized in that a) a compound of formula II

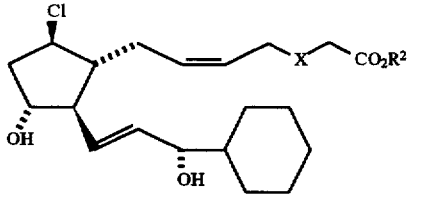

in which $R^2$ means a straight-chain or branched alkyl group with 1–6 C atoms and X has the above-indicated meaning, is hydrogenated under protection of the OH groups with dimethyl-tert-butyl silyl chloride in the presence of Pd/C and then the protective groups are removed with tetrabutylammonium fluoride trihydrate or a compound of formula II is hydrogenated in the presence of Pd/C and optionally saponified with lye and compounds with $R^1$=H are reacted with diazoalkanes of formula III

in which $R^3$ means an alkyl group with 1–6 C atoms.

The invention also relates to pharmaceutical agents based on compounds of formula I, as well as their cyclodextrin clathrates, with the usual adjuvants and vehicles.

Cyclodextrin clathrates can be obtained analogously to instructions in WO 87/05294.

The 9-chloro-prostaglandin analogues according to the invention are stable $PGD_2$ derivatives and thus valuable pharmaceutical agents, since in the case of a similar spectrum of activity, they exhibit a significantly improved (higher specificity) and mainly more prolonged action than the corresponding natural prostaglandins.

They are suitable as medicinally valuable active ingredients for use for, e.g., lowering of the blood pressure, the promotion of the blood supply of the skin, luteolysis, inhibition of gastric acid secretion, inhibition of platelet aggregation, treatment of ulcers or cytoprotection.

The compounds according to the invention can also be used in combination with, e.g., β-blockers, diuretic agents, phosphodiesterase inhibitors, calcium antagonists, thromboxane antagonists, thromboxanesynthetase and cyclooxygenase inhibitors, anticoagulant substances, such as also fibrinolytic agents, leukotriene antagonists, leukotriene synthetase inhibitors and antigestagens.

Especially suitable are the compounds according to the invention for topical use, such as, e.g., for promoting the blood supply of the skin and for lowering elevated intraocular pressure (glaucoma) as well as for promoting the renal blood circulation and for use as a diuretic agent.

In rabbits, the topical application of compounds produces a lowering of intraocular pressure.

In monkeys with experimental glaucoma, the topical application of compounds produces a normalization of the pathologically elevated intraocular pressure.

The single dose of the compounds for the use for treating elevated intraocular pressure is 1 ng–100 µg/eye, once or several times daily, if they are applied topically on human patients.

For topical application, such as, e.g., for the use for treating elevated intraocular pressure, for example, solutions, lotions or ointments are suitable.

The dose of the compounds in topical use for promoting the blood supply of the skin is 5–500 $ng/cm^2$, if they are administered to human patients.

For topical application for the use for promoting the blood supply of the skin, for example, solutions, lotions, ointments, creams or plasters are suitable.

The active ingredients according to the invention are to be used in connection with the adjuvants that are known and usual in galenicals, e.g., for the production of preparations for promoting the blood supply of the skin, for treating elevated intraocular pressure (glaucoma), for promoting renal blood circulation or for use as a diuretic agent.

The following examples are to explain the invention in more detail, without a limitation thus being made.

EXAMPLE 1

(13E)-(9R, 11R,15R)-9-Chloro-3-oxa-15-cyclohexyl-11,15-dihydroxy-16,17,18,19,20-pentanor-13-prostenoic acid-tert-butyl ester 315 mg of tetrabutylammonium fluoride trihydrate is added to a solution of 125 mg of (13E)-(9R,11R,15R)-9- chloro-3-oxa-15-cyclohexyl-11,15-bis-(tert-butyldimethylsilyloxy)-16,17,18,19,20-pentanor-13-prostenoic acid-tert-butyl ester of Example 1b) in 3 ml of tetrahydrofuran at 24° C. and stirred at this temperature for 30 hours. Then, it is diluted with diethyl ether, washed once with water and dried on sodium sulfate. After filtration, it is concentrated by evaporation in a vacuum. The residue thus obtained is purified by chromatography on silica gel. With hexane/0-100% diethyl ether, 71 mg of the title compound is obtained as colorless oil.

IR (film): 3404, 2927, 2854, 1748, 1450, 1368, 1229, 1137, 845 cm$^{-1}$.

The starting material for the title compound above is produced as follows:

1a) (5Z,13E)-(9R,11R,15R)-9-Chloro-3-oxa-15-cyclohexyl-11,15-bis-(tert-butyldimethylsilyloxy)-16,17,18,19,20-pentanor-5,13-prostadienoic acid-tert-butyl ester 136 mg of imidazole and 150 mg of tert-butyldimethylsilyl chloride are added in succession to a solution of 100 mg of (5Z,13E)-(9R,11R,15R)-9-chloro-3-oxa-15-cyclohexyl-11,15-dihydroxy-16,17,18,19,20-pentanor-5,13-prostadienoic acid-tert-butyl ester in 3 ml of dimethylformamide at 0° C. under argon. After 20 hours of stirring at 24° C., it is diluted with diethyl ether, washed with water, dried on sodium sulfate and, after filtration, concentrated by evaporation in a vacuum. The residue thus obtained is purified by chromatography on silica gel. With hexane/5-10% diethyl ether, 135 mg of the title compound is obtained as colorless oil.

IR (Film): 2928, 2855, 1750, 1472, 1368, 1255, 1127, 836, 775 cm$^{-1}$.

1b) (13E)-(9R,11R,15R)-9-Chloro-3-oxa-15-cyclohexyl-11,15-bis-(tert-butyldimethylsilyloxy)-16,17,18,19,20-pentanor-13-prostenoic acid-tert-butyl ester 125 mg of the bis-silyl ether that is produced under 1a) is dissolved in 20 ml of ethyl acetate and stirred for 2 hours in a hydrogen atmosphere with 12.5 mg of palladium (10%) on carbon at 24° C. Then, catalyst is filtered out, and it is concentrated by evaporation in a vacuum. 125 mg of the title compound thus obtained is used without further purification in the next stage.

IR (Film): 2928, 2855, 1752, 1472, 1368, 1255, 1137, 1006, 972, 899, 836, 775 cm$^{-1}$.

EXAMPLE 2

(9R,11R, 15R)-9-Chloro-3-oxa-15-cyclohexyl-11, 15-dihydroxy-16,17,18,19,20-pentanor-prostanoic acid-tert-butyl ester A solution of 100 mg of (5Z,13E)-(9R,11R,15R)-9-chloro-3-oxa-15-cyclohexyl-11,15-dihydroxy-16,17,18,19, 20-pentanor-5,13-prostadienoic acid-tert-butyl ester in 15 ml of ethyl acetate is stirred for 2.5 hours with 10 mg of palladium (10%) on carbon in a hydrogen atmosphere at 24° C. After filtration, it is concentrated by evaporation in a vacuum. The residue thus obtained is purified by chromatography on silica gel. With toluene/5% isopropanol, 92 mg of the title compound is obtained as colorless oil.

IR (Film): 3397, 2925, 2853, 1748, 1496, 1450, 1368, 1241, 1136, 970, 846, 730 cm$^{-1}$.

EXAMPLE 3

(13E)-(9R,11R,15R)-9-Chloro-3-oxa-15-cyclohexyl-11,15-dihydroxy-16,17,18,19,20-pentanor-13-prostenoic acid 1 ml of 0.5N sodium hydroxide solution is added to a solution of 60 mg of the ester, produced in Example 1), in 1 ml of methanol and stirred for 4 days at 24° C. under argon. It is then acidified to pH 4 with 1N sulfuric acid and extracted with ethyl acetate. The organic phase is washed with saturated sodium chloride solution, dried on sodium sulfate and, after filtration, concentrated by evaporation in a vacuum. In this way, 36 mg of the title compound is obtained as oil.

IR (CHCl$_3$): 3402, 2928, 2855, 1732, 1450, 1135, 973 cm$^{-1}$.

EXAMPLE 4

(9R,11R,15R)-9-Chloro-3-oxa-15-cyclohexyl-11,15-dihydroxy-16,17,18,19,20-pentanor-prostanoic acid Analogously to Example 3, 56 mg of the title compound is obtained as oil from 75 mg of the ester that is produced in Example 2).

IR (CHCl$_3$): 3418, 2930, 2855, 1732, 1450, 1135 cm$^{-1}$.

EXAMPLE 5

(13E)-(9R,11R 15R)-9-Chloro-3-oxa-15-cyclohexyl-11, 15-dihydroxy-16,17,18,19, 20-pentanor-13-prostenoic acid methyl ester An ethereal diazomethane solution is added to a solution of 18 mg of the acid, produced in Example 3), in 2 ml of methyleile chloride at 0C. under argon until permanent yellow coloring is discernible. Then, it is concentrated by evaporation in a vacuum. In this way, 18 mg of the title compound is obtained as oil.

IR (CHCl$_3$): 3414, 2928, 2855, 1734, 1448, 1374, 1110, 10.45, 1002, 892 cm$^{-1}$.

EXAMPLE 6

(9R, 11R,15R)-9-Chloro-3-oxa-15-cyclohexyl-11, 15-dihydroxy-16,17,18,19,20-pentanor-prostanoic acid ethyl ester Analogously to Example 5), 16 mg of the title compound is obtained as oil from 15 mg of the acid, produced in Example 4), with ethereal diazoethane solution. 4

IR (CHCl$_3$): 3413, 2930, 2855, 1740, 1450, 1378, 1262, 1188, 1136, 996 cm$^{-1}$.

We claim:
1. 9-Chloro-prostaglandin derivatives of formula I

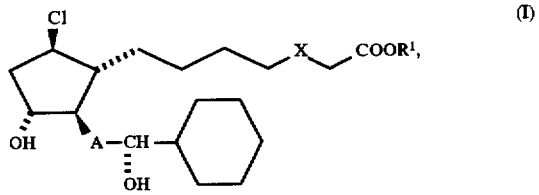

in which

X means oxygen:

R$^1$ means hydrogen or straight-chain or branched alkyl with 1–6 C atoms and

A means trans-CH=CH— or —CH$_2$—CH$_2$—, as well as their salts with physiologically compatible bases, if R$^1$ represents hydrogen, and their clathrates with α-, β- or γ-cyclodextrin.

2. (13E) -(9R,11R,15R)-9-Chloro-3-oxa-15-cyclohexyl-11,15-dihydroxy-16,17,18,19,20-pentanor-13-prostenoic acid-tert-butyl ester a compound of claim 1.

3. (9R,11R,15R)-9-Chloro-3-oxa-15-cyclohexyl-11,15-dihydroxy-16,17,18,19,20-pentanor-prostanoic acid-tert-butyl ester a compound of claim 1.

4. (13E)-(9R,11R,15R)-9-Chloro-3-oxa-15-cyclohexyl-11,15-dihydroxy-16,17,18,19,20-pentanor-13-prostenoic acid a compound of claim 1.

5. (9R,11R,15R)-9-Chloro-3-oxa-15-cyclohexyl-11,15-dihydroxy-16,17,18,19,20-pentanor-prostanoic acid a compound of claim 1.

6. (13E)-(9R,11R,15R)-9-Chloro-3-oxa-15-cyclohexyl-11,15-dihydroxy-16,17,18,19,20-pentanor-13-prostenoic acid methyl ester a compound of claim 1.

7. (9R,11R,15R)-9-Chloro-3-oxa-15-cyclohexyl-11,15-dihydroxy-16,17,18,19,20-pentanor-prostanoic acid ethyl ester a compound of claim 1.

8. A process for the production of 9-chloro-prostaglandins of formula I according to claim 1, comprising hydrogenating
a) a compound of formula II

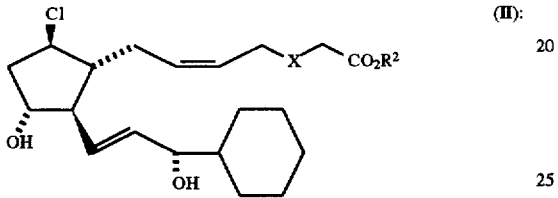

(II):

in which

R$^2$ means a straight-chain or branched alkyl group with 1–6 C atoms and

X has the above-indicated meaning, under protection of the OH groups with dimethyl-tert-butyl silyl chloride in the presence of Pd/C and removing the protective groups with tetrabutylammonium fluoride trihydrate, or hydrogenating a compound of formula II in the presence of Pd/C and optionally saponifying with lye and reacting compounds with R$^1$=H with diazoalkanes of formula III $$R^3N_2, \qquad (III)$$

in which R$^3$ means an alkyl group with 1–6 C atoms.

9. A pharmaceutical agent comprising a compound of formula I or a cyclodextrin clathrate thereof, and a pharmaceutically acceptable carrier.

10. A method for lowering blood pressure, lowering elevated intraocular pressure, promoting blood supply of the skin, luteolysis, inhibition of gastric and secretion, inhibition of platelet aggregation, treatment of ulcers or achieving a cytoprotective effect, comprising administering an effective amount of a compound of claim 1.

11. A method for treatment of glaucoma, comprising administering an effective amount of a compound of claim 1.

12. A method for promoting renal blood circulation or achieving a diuretic effect, comprising administering an effective amount of a compound of claim 1.

* * * * *